United States Patent [19]
Beattie et al.

[11] Patent Number: 5,827,741
[45] Date of Patent: Oct. 27, 1998

[54] CRYOPRESERVATION OF HUMAN ADULT AND FETAL PANCREATIC CELLS AND HUMAN PLATELETS

[75] Inventors: Gillian M. Beattie, Poway; John H. Crowe; Fern Tablin, both of Davis; Alberto Hayek, La Jolla, all of Calif.

[73] Assignee: The Regents of the University of California, Oakland, Calif.

[21] Appl. No.: 753,034

[22] Filed: Nov. 19, 1996

Related U.S. Application Data

[60] Provisional application No. 60/027,853 Oct. 3, 1996.
[51] Int. Cl.[6] ............................... A01N 1/02; C12N 5/02
[52] U.S. Cl. ............................... 435/374; 435/1.3; 435/2; 435/372; 435/375; 424/93.7; 424/93.72
[58] Field of Search ................................ 435/374, 375, 435/372, 1.3, 2; 424/93.7, 93.72

[56] References Cited

U.S. PATENT DOCUMENTS 5,510,263  4/1996  Quaranta et al. .

OTHER PUBLICATIONS

Shier, WT. Cryobiology 25:110–120, Apr. 1988.
Jindal, R and Gray, D. Transplantation. 57:317–321, Feb. 1994.
Angelini, A et al. Vox Sanguinis. 62(3):146–151, Apr. 1992.
J.H. Crowe, et al., "Preservation of Liposomes by Freeze–Drying," *Liposome Technology*, 2nd Ed., vol. I, Chap. 14 (1993) pp. 229–252.
H. Yokomise, et al., "Reliable Cryopreservation of Trachea for One Month in a New Trehalose Solution," *J. Thorac. and Cardiovasc. Surgery*, (Aug. 1995) pp. 110(2): 382–385.
T. Bando, et al., "Effects of Newly Developed Solutions Containing Trehalose on Twenty–Hour Canine Lung Preservation," *J. Thorac. and Cardiovasc. Surgery*, (Jul. 1994) pp. 108(1): 92–98.
T. Hirata, et al., "Effects of Trehalose in Preservation of Canine Lung for Transplants," *Thorac. Cardiovasc. Surgeon*, (1993) 41: 59–63.
T. Hirata, et al., "Effects of Trehalose in Canine Lung Preservation," *Surgery* (Jan. 1994) 115(1): 102–107.
G.A. Gerencser, "Cryoprotection of Aplysia Gut Basolateral Membranes by Trehalose," *Comp. Biochem, Physiol.*, (1994) 108A(1): 53–57.
A.A. Rayos, et al., "Quick Freezing of Unfertilized Mouse Oocytes Using Ethylene Glycol with Sucrose or Trehalose," *J. of Reproduction and Fertility* (1994) 100: 123–129.
T. Hirata, et al., "Successful 12–Hour Lung Preservation with Trehalose," *Transplantation Proceedings*, (Feb. 1993) 25(1): 1597–1598.
T. Bando, "Twenty–Hour Canine Lung Preservation Using Newly Developed Solutions Containing Trehalose," *Transplantation Proceedings* (Apr. 1994) 26(2): 871–872.
R.H. Foote, et al., "Fertility of Bull Spermatozoa Frozen in Whole Milk Extender with Trehalose, Taurine, or Blood Serum," *J. Diary Sci.* (1993) 76: 1908–1913.
J.H. Crowe, et al., "Preservation of Membranes in Anhydrobiotic Organisms: The Role of Trehalose," *Science* (Feb. 17, 1984) 223: 701–703.
J.H. Crowe, et al., "Is Vitrification Involved in Depression of the Phase Trabsition Temperature in Dry Phospholipid?" *Biochimica et Biophysica Acta* (1996) 1280: 187–196.
L.M. Crowe, et al., "Freeze–Dried Liposomes," *Liposomes, New Systems and New Trends in Their Applications*, Chap. 8 (1995) Editions de Sante.
L.M. Crowe, et al., "Preservation of Freeze–Dried Liposomes by Trehalose," *Archives of Biochemistry and Biophysics* (Oct. 1985) 242(1): 240–247.
L.M. Crowe, et al., "Effects of Carbohydrates on Membrane Stability at Low Water Activities," *Biochimica et Biophysica Acta*. (1984) 769: 141–150.
J.F. Carpenter, et al., "Cryoprotection of Phosphofructokinase with Organic Solutes: Characterization of Enhanced Protection in the Presence of Divalent Cations," *Archives of Biochemistry and Biophysics* (Nov. 1, 1986) 250(2): 505–512.
A.S. Rudolph et al., "A Calorimetric and Infrared Spectroscopic Study of the Stabilizing Solute Proline," *Biophys. J.* (Sep. 1986) 50: 423–430.
S.B. Leslie, et al., "Trehalose and Sucrose Protect Both Membranes and Proteins in Intact Bacteria During Drying," *Applied and Environmental Microbiology* (Oct. 1995) 61(10): 3592–3597.
J.H. Crowe, et al., "Are Freezing and Dehydration Similar Stress Vectors? A Comparison of Modes of Interaction of Stabilizing Solutes with Biomolecules," *Cryobiology* (1990) 27: 219–231.
J.H. Crowe, "Preservation of Structural and Functional Activity in Lyophilized Sarcoplasmic Reticulum," *Archives of Biochemistry and Biophysics* (Feb. 1, 1983) 220(2): 477–484.

*Primary Examiner*—David Saunders
*Assistant Examiner*—F. Pierre VanderVegt
*Attorney, Agent, or Firm*—Townsend and Townsend and Crew LLP

[57] ABSTRACT

The combination of trehalose and dimethyl sulfoxide is an unusually effective cryoprotectant for islets and islet-like cell clusters, as well as platelets. Islets and ICCs, when cooled through the thermotropic phase transition in the presence of this combination of treatment agents and then returned to physiologic temperature, retain their functionality. Likewise, platelets can be similarly cooled and warmed without undergoing premature activation. In general, trehalose can be incorporated into eukaryotic cells in general by suspending the cells in a trehalose solution and either cooling or warming the solution through the thermotropic transition of the cells.

7 Claims, 8 Drawing Sheets

CRYOPRESERVATION OF HUMAN ADULT AND FETAL PANCREATIC CELLS AND HUMAN PLATELETS

CROSS REFERENCE TO RELATED APPLICATION

This application claims the benefit of Provisional patent application Ser. No. 60/027853, filed Oct. 3, 1996, entitled "Cryopreservation of Human Adult and Fetal Pancreatic Cells," naming as inventors F. Tablin, J. H. Crowe, G. Beattie, and A. Hayek, the contents of which are incorporated herein by reference for all legal purposes to be served thereby.

BACKGROUND OF THE INVENTION

1. Field of the Invention

This invention lies in the field of cryopreservation of living cells and tissue, and of cryopreservation media.

2. Description of the Prior Art

Type I (insulin-dependent) diabetes is a widespread disease, arising from an autoimmune disorder in which insulin-secreting beta cells in the pancreas are destroyed, depriving the pancreas of its ability to secrete insulin. This impairs the body's ability to take up glucose from the blood, and the result is high glucose levels, which can lead to blindness, kidney disease, nerve damage, and ultimately death. The therapy most commonly applied is the injection of insulin to compensate for the lack of beta cells, but blood sugar levels can still fluctuate widely. Methods of lessening the fluctuations have included the use of small, frequent doses of insulin and the use of mechanical pumps that mimic the action of the pancreas, but these require the rigors of continuous or periodic maintenance, and the results are often of limited success. An alternative is a pancreatic transplant, but this requires major surgery with the attendant risk of complications, and the limited availability of donor pancreases makes this a less than viable option in general.

A more promising option is the transplantation of islets of Langerhans, using tissue derived from either cadavers or human fetuses. Islets of Langerhans are clusters of cells in the pancreas that include the insulin-secreting beta cells, and their transplantation entails considerably less risk than the transplantation of a pancreas. Sources for islet transplantation include adult pancreatic tissue, fetal pancreatic tissue and islet-like cell clusters (ICCs). Fetal tissue offers a greater content of islets in proportion to its mass, as well as a greater capacity for proliferation with its less mature cells. Islet-like cell clusters are heterogeneous cell populations that include epithelial cells that differentiate after transplantation to form various types of cells including mature islets.

Islet tissue of the various types identified above that is available for transplantation, however, is scarce, and islets must be banked and transported in order to obtain sufficient islets for a single recipient. This requires cryopreservation, and unfortunately a very low percentage of the cells are able to undergo freezing and thawing and retain their functionality. Cryoprotectants, of which dimethyl sulfoxide is the most prominently used, lessen the damage to the islets, but still entail some loss of islet functionality. This indicates a need for a cryopreservation medium that will promote the retention of a higher degree, if not all, of the islet tissue functionality upon thawing.

Platelets, or thrombocytes, are a fraction of human blood which are important contributors to hemostasis. Platelets are generally oval to spherical in shape, with a diameter of 2–4 $\mu$m, and contain about 60% protein, 15% lipid, and 8.5% carbohydrate. Included in the chemical composition of platelets are serotonin, epinephrine, and norepinephrine, each of which aids in promoting the constriction of blood vessels at the site of injury. Platelets also contain platelet factors, including platelet thromboplastin, which is a cephalin-type phosphatide, and adenosine diphosphate, both of which are important in blood coagulation. The maintenance of functional platelets is important in preserving whole blood for storage in blood banks, and in preserving concentrated platelet fractions.

The storage of platelets raises certain problems, however. While the remaining fractions of blood can be preserved by cold storage for extended periods of time, platelets tend to become activated at low temperatures and thereby useless. To avoid activation, platelets are isolated and stored separately as concentrated fractions at 22°–24° C. This raises other risks, however, namely bacterial infection as well as metabolic and enzymatic reactions known collectively as "platelet storage lesion." As a result, platelet storage is generally limited to five days. It would clearly be desirable to be able to freeze and store platelets in a manner that would result in the retention of their biological functions upon thawing.

Of additional relevance to the background of this invention is the known use of trehalose as a cryoprotectant. Trehalose is a disaccharide found in high concentrations in a wide variety of organisms that are capable of surviving complete dehydration. Trehalose is known to stabilize membranes, proteins, and prokaryotic cells during freezing and drying in vitro.

SUMMARY OF THE INVENTION

It has now been discovered that islets and islet-like cell clusters can be frozen and thawed while maintaining an unusually high level of functionality by the use of a combination of trehalose and dimethyl sulfoxide as cryoprotectants. These materials are conveniently absorbed by the cells as the cells are chilled through the thermotropic lipid phase transition temperature prior to the actual freezing of the cells. The success of the cryoprotectant combination is evident by observation of the low rate of DNA synthesis and the higher rate of insulin concentration in the cells after freezing and thawing. The use of the trehalose-DMSO combination in a cryopreservation protocol thus leads to previously unobtainable survival rates of functional human endocrine tissue.

It has further been discovered that the trehalose-DMSO combination is useful in the cryopreservation of platelets, enabling them to be frozen and thawed while retaining their ability to be activated upon the appropriate stimuli. Platelets can thus be stored for extended periods of time at temperatures sufficiently low to control bacterial infection and platelet storage lesion, without the risk of premature activation.

These discoveries have led to a further discovery, that trehalose can be incorporated into the interiors of eukaryotic cells in general whose cell walls contain a lipid bilayer, by suspending the cells in a liquid solution of trehalose and cooling or warming the suspension through the thermotropic lipid phase transition of the cells. This occurs independently of the presence or absence of DMSO.

These and other features of the invention are described in more detail below.

BRIEF DESCRIPTION OF THE FIGS.

FIGS. 1a and 1b, which do not represent data taken within the scope of this invention, are portions of the infrared spectra of islet cells taken at 0° C. and 27° C. Both temperatures are represented on each of the two spectra, the FIG. 1b spectrum representing a portion of the FIG. 1a spectrum.

FIG. 2, which also does not represent data taken within the scope of this invention, is a plot of the frequency of the peak maximum for the $CH_2$ stretch from infrared spectra of islet cells as a function of temperature, showing the temperature being varied by both cooling and warming.

FIG. 3a, which illustrates the present invention, is a plot of the frequency of the peak maximum for islet cells vs. temperature during a cooling transition as in FIG. 2, except that cooling was performed in the presence of trehalose. The plot is superimposed over plots of the amount of trehalose incorporated into the islets as a function of temperature during the same cooling transition. FIG. 3b is a plot taken from that of FIG. 3a, showing the amount of trehalose incorporated as a function of the frequency of the peak maximum.

FIG. 4, which does not represent data taken within the scope of this invention, is a fluorescence-activated cell sorting (FACS) scan of human platelets, both stimulated with thrombin and non-stimulated.

DETAILED DESCRIPTION OF THE INVENTION AND PREFERRED EMBODIMENTS

Figure 1A:
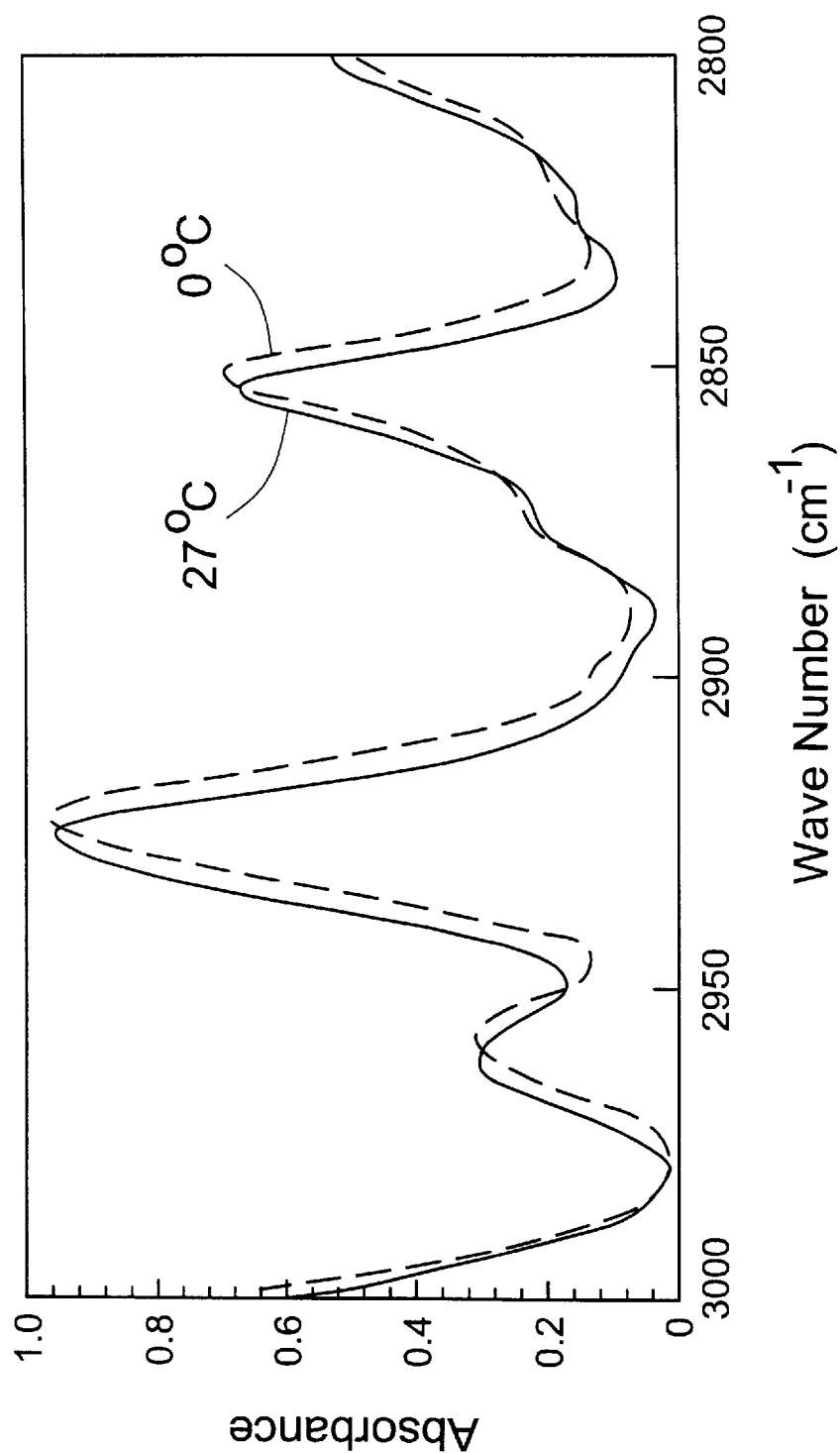

Cryopreservation in accordance with this invention is performed in a liquid cryopreservation medium that contains preservation-enhancing amounts of trehalose and DMSO. The term "preservation-enhancing amount" refers to any amount that will produce a detectable improvement in the retention of islet viability and functionality upon freezing and thawing relative to islets that have undergone freezing and thawing in the absence of a cryoprotectant. The term "islet" will at times be used in this specification to include both adult and fetal islets, as well as ICCs.

The actual amounts of trehalose and DMSO can vary, although considerations of the economical use of materials and labor, and considerations of the cryopreservation protocol, i.e., the choice of procedural steps used for cooling and thawing the islets together with the cooling and thawing rates, may affect the selection of concentration ranges that will provide the most efficient and effective preservation. In the case of trehalose, best results in most cases will be achieved at concentrations between about 10 mM and about 1,500 mM, preferably between about 100 mM and about 500 mM, in the cryopreservation medium. In the case of DMSO, best results in most cases will be achieved at concentrations between about 0.3M and about 15M, preferably between about 0.5M and about 10M, and most preferably between about 1M and about 3M.

The trehalose and DMSO are preferably dissolved in a liquid tissue culture medium, which includes any liquid solution that contains the appropriate solutes to render the solution capable of preserving living cells and tissue. Many types of mammalian tissue culture media are known in the literature and available from commercial suppliers, such as Sigma Chemical Company, St. Louis, Mo., USA; Aldrich Chemical Company, Inc., Milwaukee, Wis., USA; and Gibco BRL Life Technologies, Inc., Grand Island, N.Y., USA. Examples of media that are commercially available are Basal Medium Eagle, CRCM-30 Medium, CMRL Medium-1066, Dulbecco's Modified Eagle's Medium, Fischer's Medium, Glasgow Minimum Essential Medium, Ham's F-10 Medium, Ham's F-12 Medium, High Cell Density Medium, Iscove's Modified Dulbecco's Medium, Leibovitz's L-15 Medium, McCoy's 5A Medium (modified), Medium 199, Medium 199, Minimum Essential Medium Eagle, Alpha Minimum Essential Medium, Earle's Minimum Essential Medium, Medium NCTC 109, Medium NCTC 135, RPMI-1640 Medium, William's Medium E, Waymouth's MB 752/1 Medium, and Waymouth's MB 705/1 Medium.

In applications of this invention to the treatment of islets, the islets (the term including ICCs) can be isolated from pancreas tissue by methods known to those skilled in the art. The islets are then suspended in the cryopreservation medium (i.e., the tissue culture medium plus the added trehalose and DMSO). The concentration of the islets in the medium that will provide optimal results can vary, and the concentration selected for use in any given procedure will be governed primarily by considerations of economy and efficiency. Effective results will generally be achieved with suspensions containing from 10 to 50,000 islets per milliliter of cryopreservation medium, preferably from 100 to 10,000 islets/mL, and most preferably from 300 to 3,000 islets/mL.

The protocol for cooling the islets past the thermotropic transition temperature can be any protocol known to those skilled in the art for freezing cells of this type while avoiding damage to the cells. In preferred protocols, the islets are incubated while the temperature is lowered in stages and the DMSO and trehalose concentrations are likewise increased in stages. Adjustments to the medium are achieved by centrifugation and removal of the liquid followed by replacement of the liquid removed. The final cryopreservation medium is preferably one that provides isotonicity with the frozen cells. During thawing, the medium is replaced with a medium that does not contain DMSO, since DMSO is toxic at physiologic temperature.

The thermotropic phase transition that the islets pass through while being chilled toward the freezing temperature is a characteristic of lipid bilayers in their transition between the liquid crystalline (i.e., fluid) and gel (i.e., solid) phases. When the bilayer is in the liquid crystalline state, the lipid molecules are loosely aligned according to their hydrophilic and lipophilic regions, with the lipophilic regions facing each other, away from the aqueous environment. The loose alignment of the structure imparts flexibility to the bilayer, but the distance between the loosely aligned molecules is small enough that the permeability of the lipid bilayer is limited. Once the islets pass the phase transition temperature and assume the solidified (gel) form, the lipid molecules become scrupulously aligned and more closely packed, further limiting the permeability of the bilayer, if not eliminating it entirely. Between these two phases, however, is a transitional phase known as the thermotropic phase transition, where regions of a loosely packed liquid crystalline phase alternate with regions of a densely packed gel phase. The two phases are not fully compatible, and at locations where the two phases are adjacent to each other, the bilayer molecules form packing irregularities or defects. These packing defects cause an increase in permeability, greater than that of either the liquid crystalline phase or the gel phase. It is this increase in permeability at the locations of the packing defects that permits trehalose to pass through the bilayer and into the cells. In the practice of the present invention, therefore, trehalose is introduced into the cells by cooling the cells through the thermotropic phase transition while the cells are suspended in a liquid solution of trehalose.

The final temperature to which the islets will be cooled can vary, depending again on considerations of economy and practicality. Typical temperatures for effective storage and transport will be about 5° C. or below, preferably about 0° C. or below, and more preferably about –5° C. or below. The most preferred storage temperature is between about –40° C. and about –196° C. (the temperature of liquid nitrogen).

Once the islets have been thawed and are ready for use, transplantation is accomplished by conventional techniques known to those skilled in the art of tissue transplantation.

In applications of this invention for the cryopreservation of platelets, the platelets are first isolated and concentrated. This can be done according to conventional techniques such as those used to isolate platelets for platelet counting. According to one such technique, blood is collected in an anticoagulant, then centrifuged at a speed which is selected to produce a supernatant which is platelet-rich. Higher concentrations can be achieved by recovery of the supernatant followed by further centrifuging. Other methods are known to those skilled in the art.

Once isolated and concentrated, the platelets are suspended in a solution containing the trehalose-DMSO combination. The solvent can be a tissue culture medium such as those listed above for use with islets, or any other medium that will not cause damage to the platelets. The concentration of platelets in the suspension can vary. In most cases, appropriate concentrations for efficient and economical cryopreservation will be from about $10^6$ to about $10^{10}$ cells/mL, preferably from about $10^7$ to about $10^9$ cells/mL, and most preferably about $10^8$ cells/mL.

The platelets can be maintained in suspension at 22° C. until ready for preservation. While the freezing and thawing protocols and the methods of incorporating trehalose can vary, a presently preferred method is to cool the platelet suspension at 1° C. per minute to a final temperature of –70° C., then to transfer the cooled platelets to liquid nitrogen. The platelets can be stored in liquid nitrogen for as much as 32 days or more.

As they are being cooled, the cells pass through the thermotropic liquid phase transition, which occurs between 15° C. and 20° C. Passage through this phase transition will result in the passage of the trehalose through the platelet membrane and into the interior of the platelets due to the transitory increase in membrane permeability as described above. Other means of incorporating trehalose into the platelets to achieve an equivalent result will be readily apparent to those skilled in the handling of platelets. A preferred final temperature for storage purposes is within the range of about –70° C. to about –196° C.

When platelets that have been chilled below their thermotropic phase transition temperature are needed for clinical use, the platelet pellet will be rapidly thawed at 37° C. to an ice ball and progressively diluted until ready for use. It is preferred that the DMSO be removed from the platelets and the suspending medium before the platelets are returned to physiologic temperature. Dilution is preferably performed in two or more, preferably four or more, volumes of buffer per volume of sample.

The incorporation of trehalose into eukaryotic cells independently of cryopreservation, and independently of the presence or absence of DMSO, is achieved in accordance with this invention by suspending the cells in a liquid solution of trehalose and cooling or warming (preferably cooling) the suspension through the thermotropic phase transition. While this specification provides examples in which this discovery is applied to islets, ICCs and platelets, these examples lead to the conclusion that trehalose incorporation by this technique is applicable to any eukaryotic cells or cell-like structures that contain a lipid bilayer in the cell membrane. Any liquid solution of trehalose can be used, although the tissue culture media cited above are preferred for purposes of protecting the cells during the phase transition. Likewise, the concentration of trehalose in the suspending solution is not critical and can vary. Nevertheless, the preferred concentrations are those cited above. Cooling or warming is performed at a rate slow enough to permit the passage of the trehalose through the disrupted bilayer, although the actual cooling rate is not critical. Effective rates are readily determined by analyzing the cells for trehalose content, using methods well known in the art. Examples of such methods are those used in the examples below. For cooling, preferred rates are those cited above. When the temperature transition is a cooling transition, the retention of the trehalose in the cells upon rewarming of the cells above the phase transition temperature, and to physiologic temperature if desired, is readily achieved by rewarming at a rapid rate, i.e., a rate that is fast enough to prevent loss of the entire amount of trehalose present in the cell interiors. Retention is alternately achieved by rewarming the cells while suspended in a solution of trehalose, thereby eliminating the concentration gradient that would otherwise cause outward diffusion of the trehalose.

The term "eukaryotic cell" is used herein to mean any nucleated cell, i.e., a cell that possesses a nucleus surrounded by a nuclear membrane, as well as any cell that is derived by terminal differentiation from a nucleated cell, even though the derived cell is not nucleated. Examples of the latter are terminally differentiated human red blood cells. Mammalian, and particularly human, eukaryotes are preferred.

The following examples are offered for purposes of illustration only.

EXAMPLES

Materials and Methods

All procedures referred to below but not explained are documented in published literature and known to those skilled in the art. All materials whose source is not given below are readily available from commercial suppliers who are also known to those skilled in the art.

1. Tissue

Human fetal pancreases were provided by the Anatomic Gift Foundation (Laurel, Md., USA) and Advanced Bioscience Resources (Oakland, Calif., USA) after the termination of pregnancy by dilatation and extraction between 18 and 24 weeks of gestation. Gestational age was determined by several criteria including bi-parietal diameter, femur length and fetal foot measurement. Warm and cold ischemic times were approximately 5 minutes and 24 hours, respectively. For tissue culture, the pancreases were digested with collagenase and cultured as islet-like cell clusters (ICCs), as described by Beattie, G. M., et al., *Transplantation* 56:1340 (1993), and Beattie, G. M., et al., *J. Clin. Endocrinol. Metab.* 78:1232 (1994), the disclosures of which are incorporated herein by reference. Human adult islets were isolated with an automated method and further purified by handpicking single islets, 50–100 microns in diameter, after dithizone staining.

2. Lipid Phase Transitions

Lipid phase transitions were measured by changes in membrane $CH_2$ vibrational frequency, using a Perkin-Elmer Fourier transform infrared microscope coupled to a Perkin-Elmer 1620 FTIR optical bench and equipped with a temperature controller. Data manipulations were limited to baseline adjustment and absorbance expansion, using the flat and abex routines in Perkin-Elmer IRDM software. Samples were prepared by placing the islets between $BaF_2$ windows, with a 10-micron spacer supporting the windows, and placing the windows and islets in the temperature controller on the microscope stage. All curve fitting was done by multiple iterations of a least squares algorithm on a microcomputer.

3. Introduction of Trehalose Into Cells

It is well known that membranes undergo transient elevations in permeability as they pass through thermotropic lipid phase transitions. In the procedures reported in these examples, the elevated permeability was used as a means of introducing trehalose into islets and ICCs. The introduction of trehalose was confirmed by use of $[^{14}C]$-trehalose as a tracer. Single cell suspensions of islets or ICCs were prepared in a trehalose solution, and the suspensions were cooled at a rate of 1° C./min through the phase transition temperature. The cells were then filtered from the trehalose solution through a Millipore filter, which was then transferred to a liquid scintillation vial where the tracer was detected by liquid scintillation counting which indicated the presence of trehalose in the cells, thereby confirming that the procedure had indeed resulted in introduction of trehalose into the cells.

4. Cryopreservation and Thawing Procedures

The ICCs and islets were frozen in two groups each, one using DMSO as the sole cryopreservative and the other using both DMSO and trehalose as combined cryopreservatives. The first medium consisted of RPMI-1640 plus 10% human serum containing 11.1 mM glucose (serving as a cell nutrient) and 2M DMSO; this medium is referred to herein as "CDG." The second medium consisted of RPMI-1640 plus 10% human serum containing 2M DMSO and 300 mM trehalose, and is referred to herein as "CDT." Except for the use of 11.1 mM glucose in one case and 300 mM trehalose in the other, the freezing and thawing protocols were the same in each case, and were as follows.

One thousand ICCs (or islets) were transferred to 0.2 mL of a solution of RPMI-1640 plus 10% normal human serum containing saccharide (either 11.1 mM glucose or 300 mM trehalose) in each of a series of 100 mm reusable sterile Kimble glass tubes with phenolic caps. To these ICCs or islets were then added 0.1 mL of RPMI-1640 plus 10% normal human serum containing 2 M DMSO and either 11.1 mM glucose or 300 mM trehalose, and the resulting mixture was incubated for 5 minutes at 24° C. An additional 0.1 mL of the same solution was added, and incubation was continued for an additional 25 minutes at 24° C. This was followed by addition of 0.4 mL of medium further containing 3 M DMSO and either 11.1 mM glucose or 300 mM trehalose at 4° C., and incubation for 15 minutes on ice. The mixture was then supercooled in an alcohol bath to −7.5° C., and allowed to rest for 5 minutes. To cause nucleation, the outside of each tube was then touched at the level of the meniscus in the tube with a metal rod that had been dipped in liquid nitrogen, and the latent heat of fusion was allowed to dissipate for ten minutes. The tubes were then cooled to −40° C. at a rate of 0.25°–0.3° C./min, and stored in liquid nitrogen (−196° C.).

When the ICCs and islets were ready to be thawed, the tubes were partially thawed rapidly at 37° C. to an ice ball and transferred to ice. The cells were then quickly pelleted by centrifugation for one minute, whereupon the supernatant was carefully removed and 1 mL of a cold solution containing RPMI-1640 plus 10% human serum and the saccharide (either trehalose at 300 mM trehalose or sucrose at 750 mM) was added to the pellet. The resulting mixture was kept on ice for thirty minutes. This was followed by addition of 1 mL of RPMI-1640 plus 10% human serum (the cryopreservation medium without either DMSO or saccharide) with incubation for five minutes at room temperature, an additional 1 nL of the same DMSO- and saccharide-free medium with incubation for an additional five minutes at room temperature, an additional 2 mL of the DMSO- and saccharide-free medium with incubation for an additional five minutes at room temperature, and an additional 4 mL of the DMSO- and saccharide-free medium with incubation for an additional five minutes at room temperature. Finally, the cells were centrifuged, transferred to more of the DMSO- and saccharide-free medium and incubated at 37° C.

Cell functionalities retained by ICCs and islets that had undergone freezing and thawing in the presence of the two cryopreservation media (i.e., those containing DMSO and saccharide) were compared with the functionalities of ICCs and islets that had been cultured in RPMI-1640 plus 10% human serum (i.e., those containing neither DMSO nor saccharide), and had not undergone freezing and thawing. The latter are referred to in the examples as "fresh" ICCs and islets. Freezing and thawing was also performed using a medium that was identical to CDT except that it did not contain DMSO, i.e., its composition was RPMI-1640 plus 10% human serum containing 300 mM trehalose. The protocol in this case was identical to that used for CDT.

5. In Vitro Viability and Function

Three days after thawing, viability and functionality of cryopreserved/thawed tissue were assessed by examining DNA and insulin content, and insulin release in response to secretagogues (16.7 mM glucose for adult islets and 10 mM theophylline for ICCs). The DNA content of cell sonicates was measured by fluorometry. Before the assay was performed, the ICCs were briefly exposed to 100 $\mu$g/mL DNAse (Sigma Chemical Co., St. Louis, Mo., USA) and washed three times with phosphate-buffered saline (PBS) to remove any DNA from dying cells that had not survived the cryopreservation process. Immunoreactive insulin was assayed in the medium and in acid ethanol extracts of cell sonicates using a solid phase radioimmunoassay. Incorporation of $[^3H]$-thymidine (64 Ci/mmol) into cellular DNA was determined by measuring trichloroacetic acid precipitable counts in a scintillation counter.

6. Transplantation Procedures

The animals used in the transplantation studies were NIH Swiss homozygous athymic nude mice obtained through the NIH-Grantee Reimbursement Program from the Charles River Breeding Laboratories (Charles River, Mass., USA), and were housed in microisolater cages in a semi-sterile room where they were maintained according to NIH guidelines.

The animals were sacrificed three months after transplantation, and the kidneys removed. The kidneys were then fixed in 4% paraformaldehyde, and 5-micron sequential sections were stained using hematoxylin and eosin and the immunoalkaline phosphatase technique. The primary antibody used was guinea pig anti-porcine insulin. Normal rabbit serum was used as the control serum. As an alternative means for quantification of insulin, the grafted human tissue was carefully peeled away from the kidney under direct vision, then minced finely, homogenized in distilled water and sonicated. Aliquots of the sonicates were extracted with acid ethanol for insulin radioimmunoassay and dried for DNA quantitation as described above for the in vitro assays.

7. Statistical Analyses

The statistical significance of observed differences was analyzed by Student's "t" test for unpaired data when two groups were involved. Multiple comparisons were done with ANOVA and Fischer's protected least significance difference test using 95% level as the limit of significance.

EXAMPLE 1

This example is an illustration of the prior art, and shows the hysteresis observed between cooling islet cells through the lipid phase transition and warming the cells through the transition.

Figure 1B:
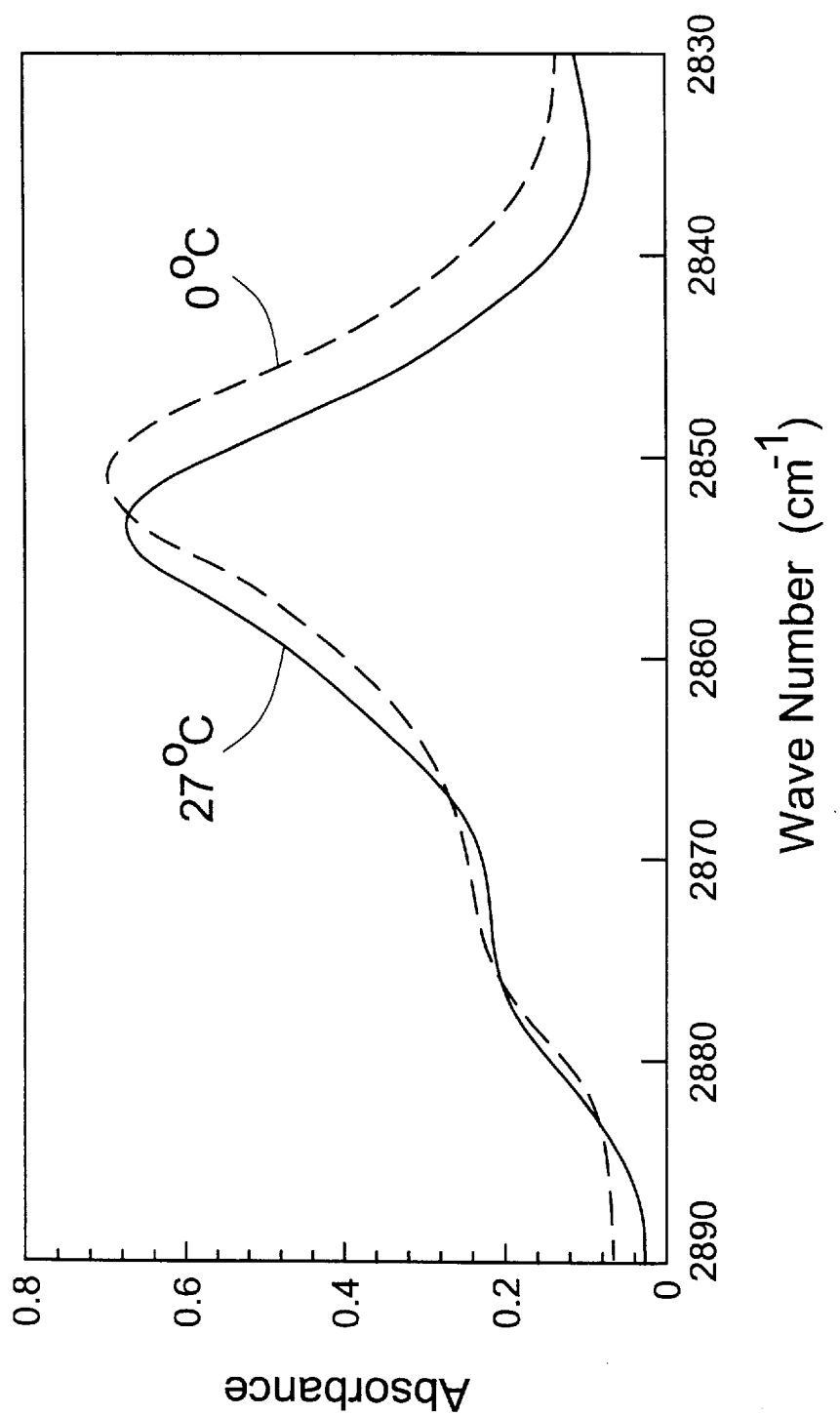
Figure 2:
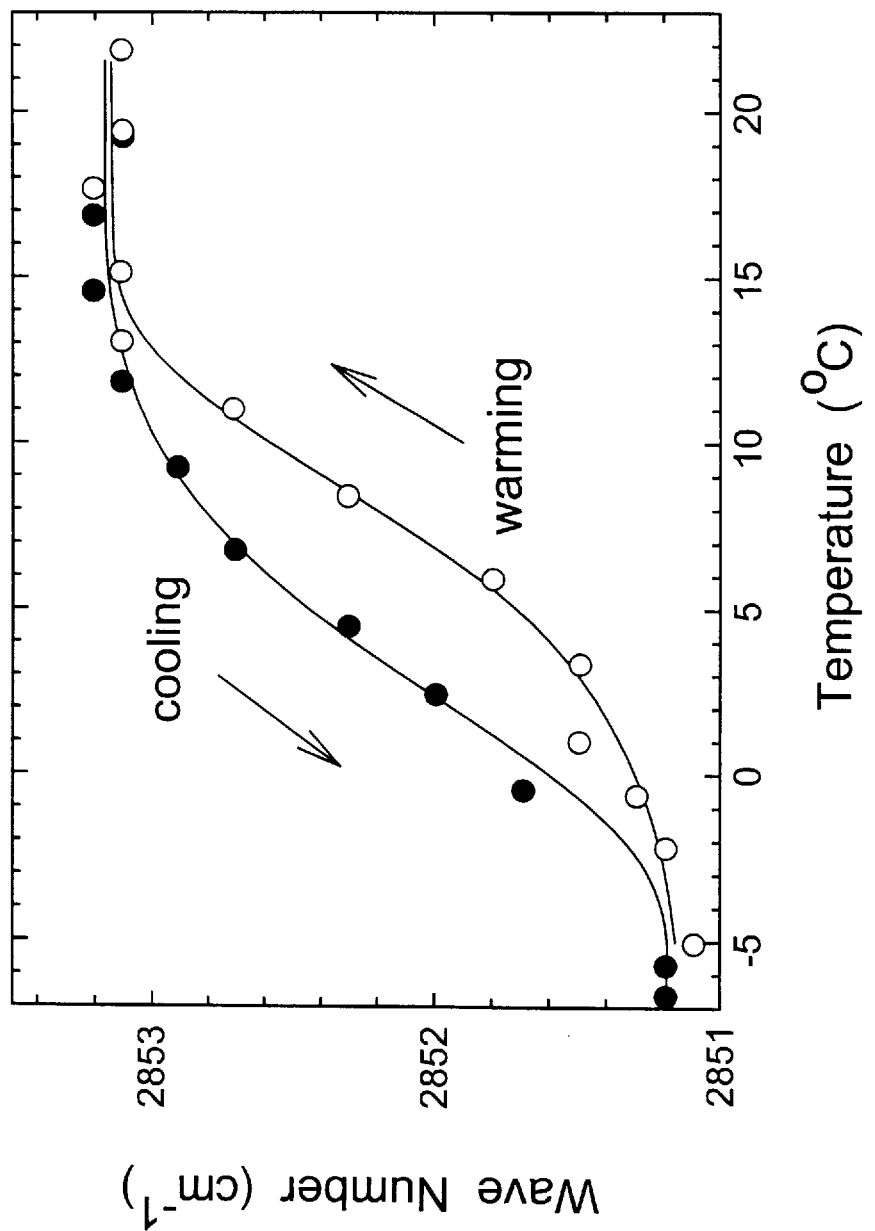

Typical infrared spectra in the hydrocarbon chain stretching region in islet cells both before and after a phase transition are shown in FIGS. 1a and 1b, where FIG. 1b is an expansion of a portion of the horizontal scale of FIG. 1a. Spectra were taken both above the transition temperature (i.e., at 27° C., represented by the solid line in both Figures) and below the transition temperature (i.e., at 0° C., represented by the dashed line in both Figures), with no cryopreservation agent having been used. The $CH_2$ stretch near 2850 $cm^{-1}$ is conveniently used to measure phase transitions in biological membranes, hence the expansion of the portion surrounding this band in FIG. 1b. The frequency of the maximum for this band was determined as a function of temperature, first during a cooling transition and then during a re-warming transition. The results are plotted in FIG. 2, where the filled circles (●) represent the cooling transition and the open circles (○) represent the warming transition. The plot shows that during cooling the frequency of this band falls from about 2853 $cm^{-1}$ to about 2851 $cm^{-1}$, with a midpoint at about 5° C. The re-warming transition has the same end frequencies, but the midpoint of the curve shifts to about 9° C., indicating a hysteresis of about 4° C. The cooling and re-warming were then repeated, and the same shift in curve midpoint was observed.

EXAMPLE 2

This example shows the correlation between the passage of trehalose into cells and the location of the cells on the absorption peak wave number vs. temperature curve. The cells used in this test included both islets from adults and ICCs from fetuses.

Figure 3A:
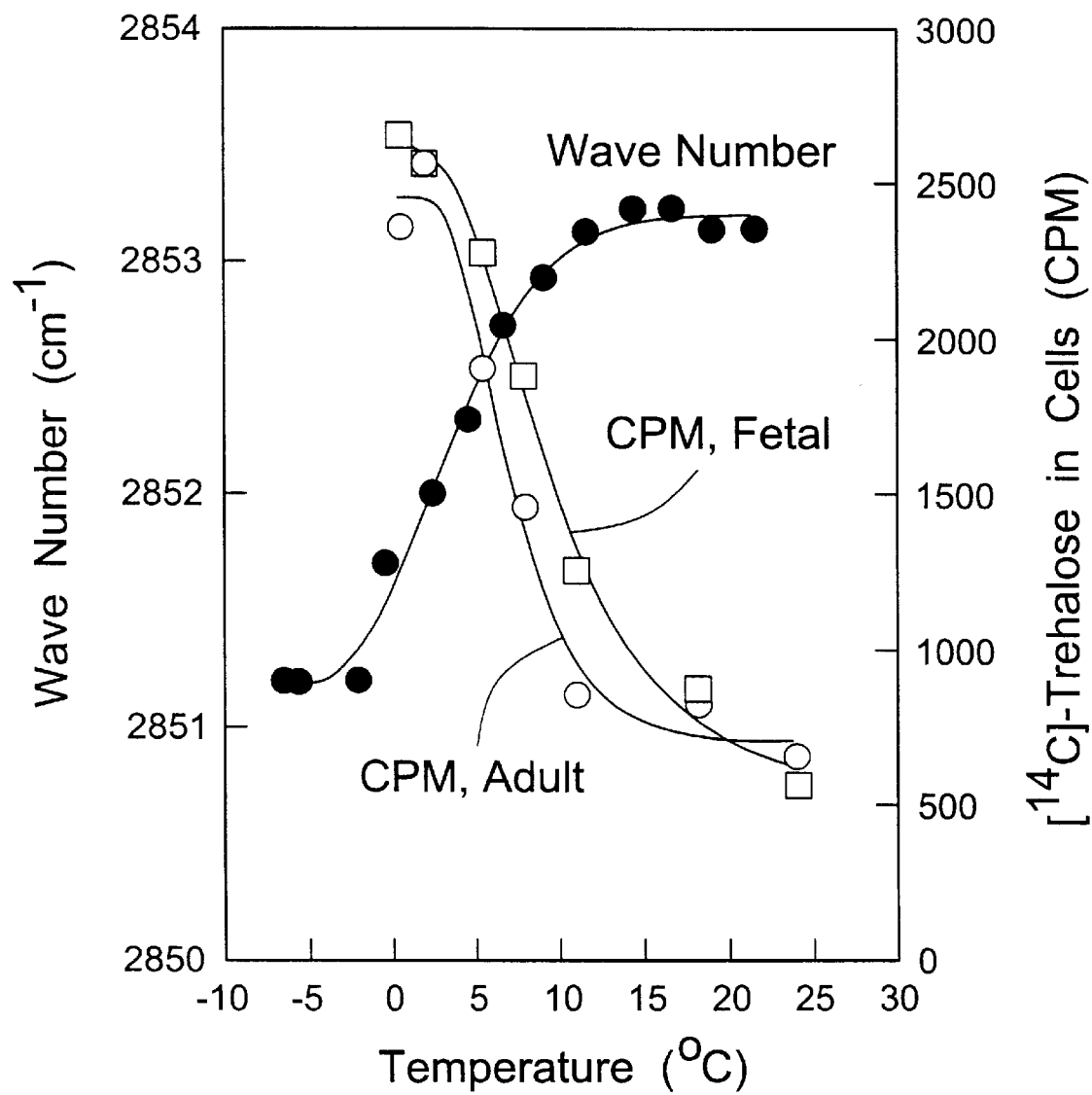

As described in part 3 of the Materials and Methods section above, the cells were suspended in CDT and the suspension was gradually cooled below the phase transition of the cells. The phase transition of the cells was monitored by recording the wave number of the band maximum for the $CH_2$ stretch, and the amount of trehalose entering the cells was determined by liquid scintillation counting. The results are plotted in FIG. 3a, where the filled circles (●) represent the wave number and hence the phase transition, the open circles (○) represent the amount of trehalose in the adult islets, and the open squares (□) the amount of trehalose in the fetal islets. The plot shows that the entry of trehalose coincides with the phase transition, and the trehalose reaches maximal values as the transition is completed. Above the phase transition, i.e., at temperatures above about 15° C., only minimal amounts of trehalose had entered the cells.

Figure 3B:
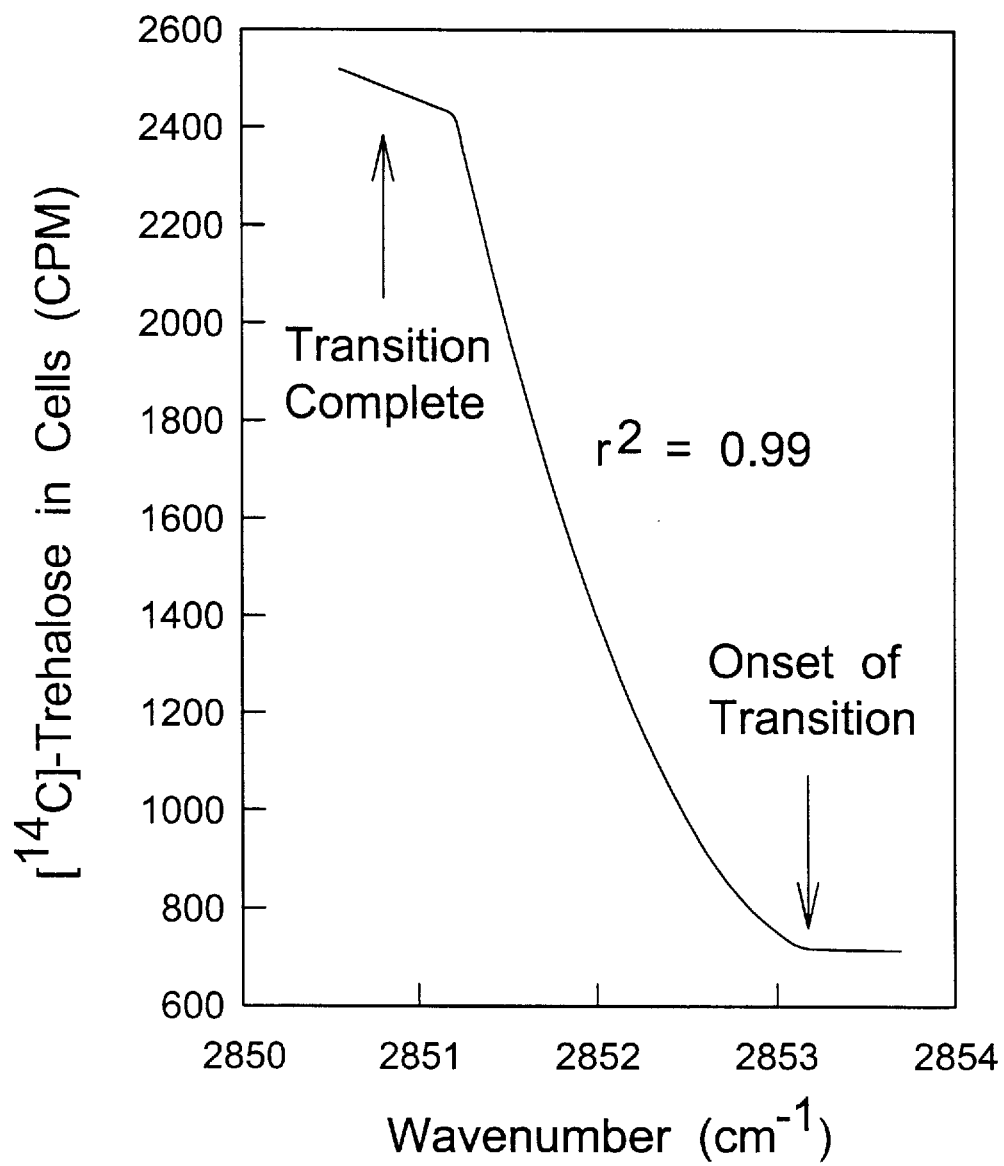

These results are presented as a plot of trehalose incorporation vs. wave number of the band maximum for the fetal ICCs in FIG. 3b. The curve shows that the two parameters are clearly related, with more than 99% of the influx of trehalose occurring during the phase transition.

EXAMPLE 3

This example presents in vitro test results on adult islets, with a comparison between results obtained using a cryopreservation medium containing trehalose in accordance with this invention (CDT), and those obtained with a medium containing glucose rather than trehalose (CDG).

Freezing and thawing of adult islets in both media were performed as described above. Three days after thawing, the islets were assayed for insulin and DNA content, and for insulin release following stimulation with 16.7 mM glucose, as compared to a basal glucose concentration of 1.6 mM. Assays were also performed on islets that were not treated with either medium and had not undergone freezing and thawing. The results are shown in Table I below.

TABLE I

In Vitro Test Results on Adult Islets

|  | Fresh | Cryopreserved with: CDG | CDT |
|---|---|---|---|
| Total DNA (μg) | 2.4 ± 0.2 | 1.4 ± 0.1 | 2.2 ± 0.1 |
| Insulin content (pmoles/μg DNA) | 43.7 ± 2.4 | 46.6 ± 6.5 | 56.5 ± 7.9 |
| Insulin release (pmoles/μg DNA): |  |  |  |
| 1.6 mM Glucose | 1.2 ± 0.1 | 2.3 ± 0.2 | 1.3 ± 0.2 |
| 16.7 mM Glucose | 2.5 ± 0.2 | 5.7 ± 0.6 | 3.2 ± 0.6 |
| Stimulation delta | 2.1 ± 0.2 | 2.6 ± 0.3 | 2.4 ± 0.2 |

This table shows that the recovery of adult islets in terms of DNA content after cryopreservation with CDT was 92% of control, while recovery after cryopreservation with CDG was 58% of control. Basal and glucose-stimulated insulin release values were both higher in islets cryopreserved with CDG than they were in islets cryopreserved with CDT, but the stimulation delta values obtained with the two media were similar, as were the insulin contents.

EXAMPLE 4

This example presents in vitro test results on fetal ICCs, again comparing results obtained using a cryopreservation medium containing trehalose (CDT) with those obtained with a medium containing glucose rather than trehalose (CDG).

Freezing and thawing of fetal ICCs in both media were performed as described above. Three days after thawing, the ICCs were assayed for insulin and DNA content, and for [$^3$H]-thymidine incorporation and insulin release following stimulation with 16.7 mM glucose and 10 mM theophylline, and with a basal glucose concentration of 1.6 mM. Assays were also performed on islets that were not treated with either medium and had not undergone freezing and thawing. The results are shown in Table II below.

TABLE II

In Vitro Test Results on Fetal ICCs

| | Fresh | Cryopreserved with: | |
|---|---|---|---|
| | | CDG | CDT |
| Total DNA (μg) | 3.1 ± 0.1 | 1.3 ± 0.4 | 2.9 ± 0.3 |
| [$^3$H]-Thymidine incorporation (cpm/μg DNA) | 1030. ± 40 | 7833. ± 2775 | 1378. ± 154 |
| Insulin content (pmoles/μg DNA) | 2.2 ± 0.3 | 0.4 ± 0.1 | 2.3 ± 0.4 |
| Insulin release (fmoles/μg DNA): | | | |
| 1.6 mM Glucose | 69. ± 24 | 49. ± 13 | 39. ± 8 |
| 16.7 mM Glucose + 10 mM Theophylline | 134. ± 37 | 126. ± 16 | 139. ± 37 |
| Stimulation delta | 3.5 ± 0.7 | 3.8 ± 0.6 | 6.4 ± 2.4 |

The data in this table show that the recovery of fetal ICCs in terms of DNA content after cryopreservation with CDT was 94% of control, while recovery after cryopreservation with CDG was 42% of control. Incorporation of [$^3$H]-thymidine into nuclear DNA was increased after cryopreservation with CDG, but the result with CDT was similar to the control. The insulin content was markedly reduced in the CDG-preserved cells, but not in the CDT-preserved cells. Comparison between basal insulin release and glucose- and theophylline-stimulated insulin release was inconclusive, and the stimulation delta was higher in the CDT-preserved cells.

EXAMPLE 5

This example is a repeat of the experiment reported in Example 4, showing the synergistic effect of DMSO and trehalose. In vitro tests on fetal ICCs were performed, in one group of tests using CDT as defined above, in another using the same medium minus the DMSO (i.e., containing trehalose as the only cryoprotectant), and in a third using the CDG as defined above (i.e., in which DMSO was the only cryoprotectant). Total DNA was assayed three days after thawing, as in Example 4, and the results were as follows:

Total DNA in ICCs cryopreserved with DMSO and trehalose: 96%±6.3% relative to fresh ICCs Total DNA in ICCs cryopreserved with trehalose alone: 19%±3.8% relative to fresh ICCs Total DNA in ICCs cryopreserved with DMSO alone: 35±9% relative to fresh ICCs In each case, the number of samples was 4 (n=4), and $p<0.0001$. The results obtained with the combination of the two cryoprotectants far exceed the sum of the results obtained with the individual cryoprotectants, and synergism is thus well established.

EXAMPLE 6

This example presents in vivo test results obtained by transplanting adult islets and fetal ICCs into mice, followed by measurements of the insulin content of the grafts. Cells cryopreserved in CDT were compared with those cryopreserved in CDG and with fresh cells (that had not undergone freezing).

Equivalent numbers of fresh and cryopreserved and thawed adult islets and fetal ICCs were transplanted under the kidney capsules of nude mice. Three months after transplantation, the grafts were removed. Those preserved with CDT were observed to be much larger than those preserved with CDG. Sections were immunostained by the alkaline phosphatase method with guinea pig anti-porcine insulin as the primary antibody. Observation by microscope indicated that the grafts preserved with CDT contained more insulin-positive cells than those preserved with CDG. Total insulin contents of acid ethanol extracts of the grafts were determined by radioimmunoassay. The results are shown in Table III below where they are compared with equivalent results obtained on aliquots of tissue before transplantation.

TABLE III

In Vivo Test Results on Adult Islets and Fetal ICCs

| | Insulin Content in pmoles | | | |
|---|---|---|---|---|
| | Before | After Transplantation | | |
| | Trans- | | Cryopreserved with: | |
| | plantation | Fresh | CDG | CDT |
| Adult islets (n = 400) | 400 | 147 ± 5 | 14 ± 1 | 200 ± 9 |
| Fetal ICCs (n = 400) | 20 | 490 ± 99 | 29 ± 3 | 447 ± 85 |

The data in Table III show that grafts from adult islets cryopreserved with CDT contained 14–15 times more insulin than grafts from adult islets cryopreserved with CDG. Grafts of fetal ICCs contained more than twice as much insulin as grafts of equivalent numbers of adult islets.

EXAMPLE 7

This example investigates thrombin-induced activation of human platelets, and illustrates the ability of the DMSO-trehalose combination to preserve the ability of the platelets to respond to thrombin after having been frozen and thawed.

Human platelets were isolated from whole blood by low-speed differential centrifugation. The platelets were washed free of plasma proteins, suspended in the CDT cryopreservation medium at a concentration of $10^8$ cells/mL, cooled at a rate of 1° C./min to −70° C., held overnight, then transferred to liquid nitrogen where they were held for 32 days. The platelets were then thawed according to the protocols described above. The platelets were then treated with thrombin (a physiological platelet agonist), and analyzed for P-selectin (GMP-140) on the platelet surface. P-Selectin is an alpha granule membrane protein that is present on the platelet surface only upon activation of the platelets, and that therefore serves as an activation marker. Analysis for P-selectin was performed by fluorescence-activated cell scanning (FACS).

Figure 4:
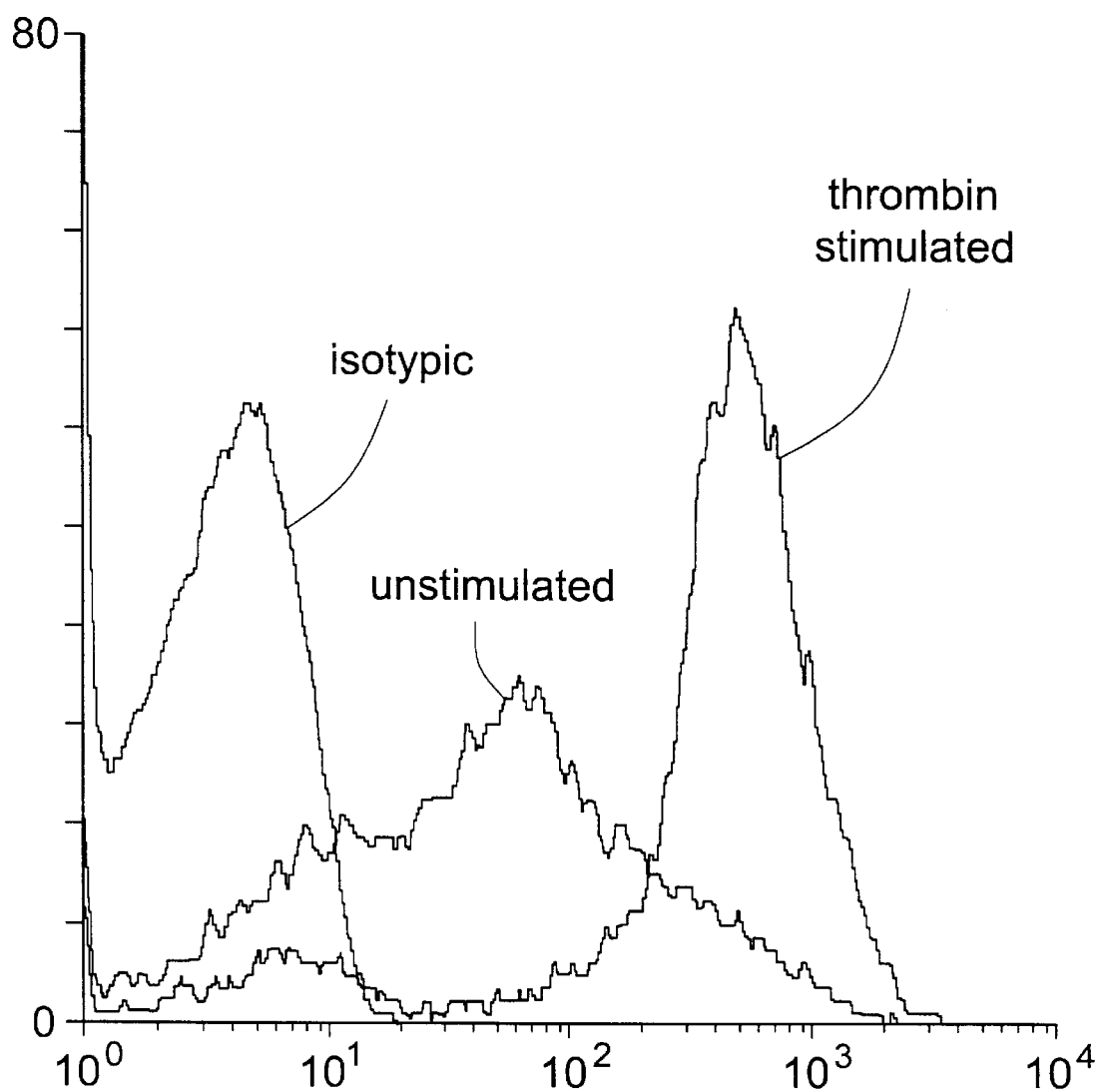
Figure 5:
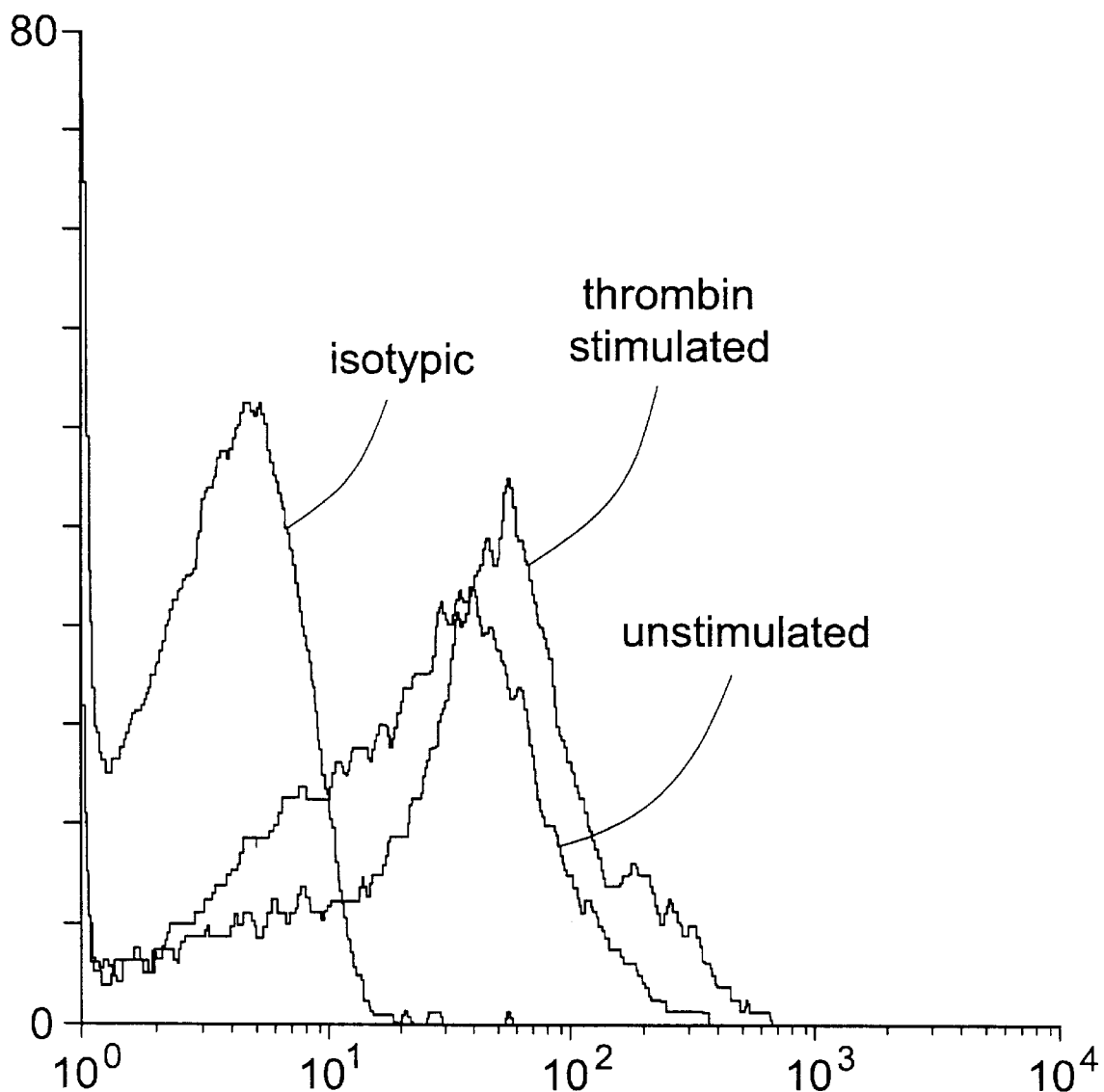
FIG. 5 is a FACS scan illustrating the invention, showing corresponding data on platelets that have been frozen in the presence of a cryopreservation medium containing trehalose and DMSO.

The FACS curves appear in FIGS. 4 and 5. FIG. 4 represents fresh washed platelets that have not undergone freezing and thawing, while FIG. 5 represents washed platelets that have been frozen and thawed in the presence of CDT medium. In both Figures, the curve labeled "Isotypic" shows the level of non-specific background fluorescence. The remaining two curves represent the platelets that have not been stimulated by thrombin (labeled "Unstimulated") and those that have been stimulated by thrombin (labeled "Thrombin Stimulated"). In the fresh cells (FIG. 4), the thrombin stimulation causes an increase in the number of cells that express P-selectin. In the frozen and thawed cells, the thrombin stimulation still causes an increase in the number of cells expressing P-selectin, although the increase is less than that observed in the fresh cells. By comparison, in prior studies of platelet activation, i.e, in the absence of the DMSO-trehalose combination, stimulation after a freeze-thaw cycle produced no platelet activation at all.

EXAMPLE 8

This example illustrates the incorporation of trehalose into human platelets as the platelets are cooled through the thermotropic phase transition.

Human platelets were washed as in Example 7, then suspended at room temperature in a cryopreservation medium consisting of RPMI-1640 plus 10% human serum and 300 mM trehalose (DMSO was not present), the trehalose including [$^{14}$C]-trehalose as a tracer. The suspension was then cooled at a rate of 1° C./minute from room temperature to 4° C. During the chilling, aliquots of the suspension were removed and rapidly filtered on Millipore filters, and the filtered platelets were transferred to scintillation vials. Scintillation cocktail (a mixture of organic solvents) was added to each sample, and the radioactivity in each sample was determined by liquid scintillation counting. Separately, infrared spectra of human platelets were taken at various points during an identical cooling protocol, and the wave number of the band maximum for the CH$_2$ stretch was recorded as a function of temperature.

Figure 6:
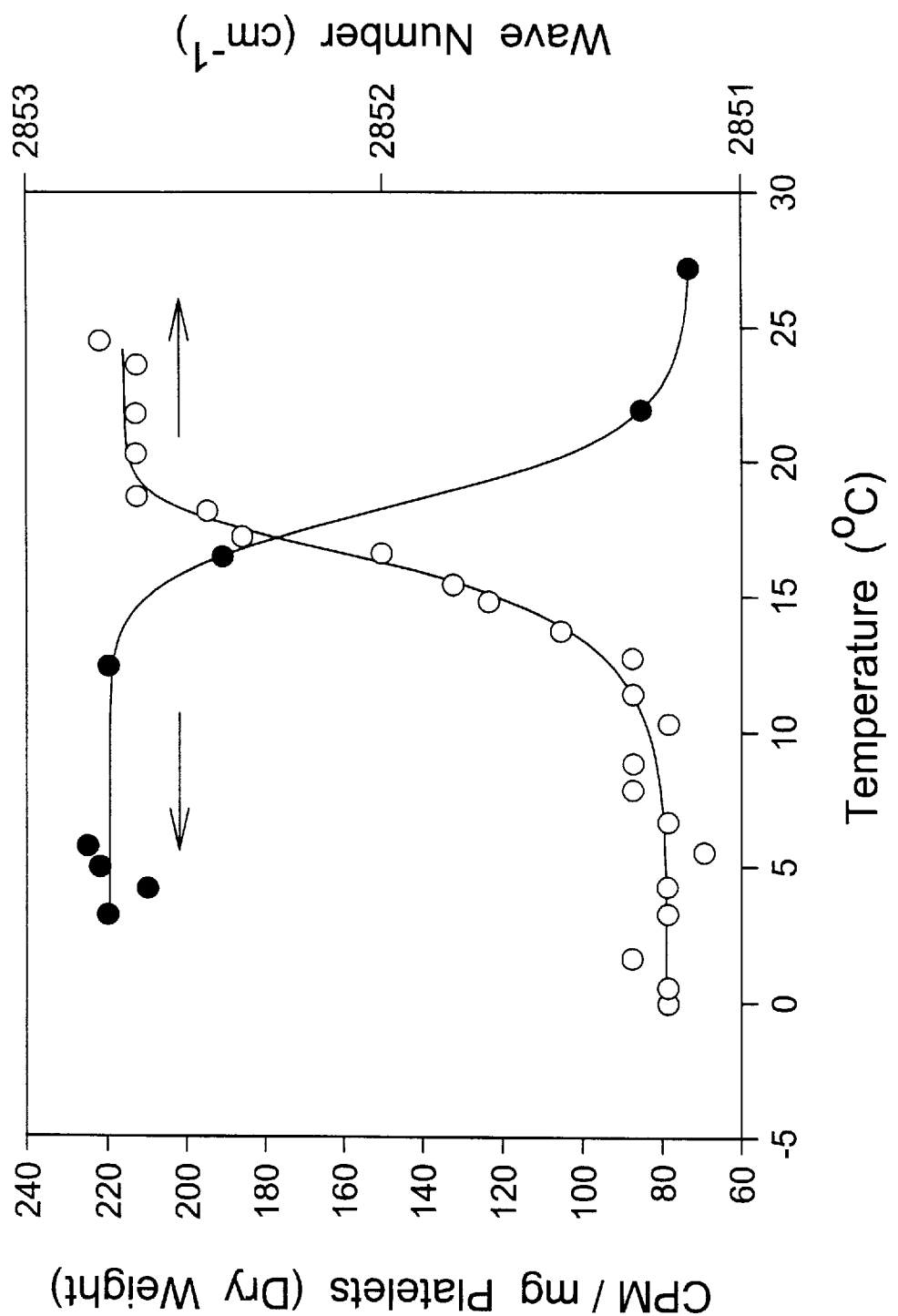
FIG. 6 is a graph showing two plots superimposed—a plot of the frequency of the peak maximum of the $CH_2$ stretch in an infrared spectrum of human platelets vs. temperature as the platelets are being cooled, and a plot of the amount of trehalose incorporated into the platelets as a function of temperature during the same cooling transition.

The radioactivity of the filtered cells (representing the amount of trehalose incorporated into the cells) and the wave number of the band maximum, both taken during the cooling procedure, are plotted as a function of temperature in FIG. 6, where the filled circles represent the radioactivity in counts per minute per milligram of platelets (dry weight) and the open circles represent the wave number. The plot shows that the transition points of the two curves occur approximately at the same temperature, and that trehalose is in fact incorporated in the cell interiors as an result of the phase transition.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

We claim:

1. A method for incorporating trehalose into the interiors of eukaryotic cells containing lipid bilayers, said method comprising subjecting said cells to a temperature change through their thermotropic lipid-phase transition temperature while said cells are suspended in a liquid solution of trehalose in the absence of DMSO, said temperature change occurring at a rate that permits passage of trehalose through said bilayers.

2. A method in accordance with claim 1 comprising cooling said cells through said thermotropic lipid-phase transition temperature.

3. A method in accordance with claim 1 in which said cells are selected from the group consisting of platelets, islets of Langerhans, and islet-like cell clusters.

4. A method in accordance with claim 1 in which said cells are platelets.

5. A method in accordance with claim 1 in which said cells are selected from the group consisting of islets of Langerhans, and islet-like cell clusters.

6. A method in accordance with claim 1 in which said liquid solution of trehalose contains trehalose in an amount ranging from about 10 mM to about 1,500 mM.

7. A method in accordance with claim 1 in which said liquid solution of trehalose contains trehalose in an amount ranging from about 100 mM to about 500 mM.

* * * * *